United States Patent [19]

Degner et al.

[11] 4,431,490
[45] Feb. 14, 1984

[54] PREPARATION OF CYCLOPENTADECANOLIDE

[75] Inventors: Dieter Degner, Dannstadt-Schauernheim; Werner Hoffmann, Neuhofen; Frank Thoemel, Weinheim, all of Fed. Rep. of Germany

[73] Assignee: BASF Aktiengesellschaft, Ludwigshafen, Fed. Rep. of Germany

[21] Appl. No.: 392,541

[22] Filed: Jun. 28, 1982

[30] Foreign Application Priority Data

Jul. 10, 1981 [DE] Fed. Rep. of Germany ....... 3127242

[51] Int. Cl.³ .............................................. C25B 3/04
[52] U.S. Cl. .................................... 204/59 R; 204/75
[58] Field of Search ................................ 204/59 R, 75

[56] References Cited

U.S. PATENT DOCUMENTS 3,444,059  5/1969  Throop .................................. 204/72

Primary Examiner—F. Edmundson
Attorney, Agent, or Firm—John H. Shurtleff

[57] ABSTRACT

Cyclopentadecanolide of the formula I

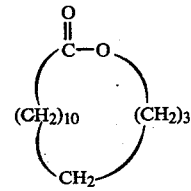

is prepared by a process wherein 12-oxocyclopentadecanolide of the formula

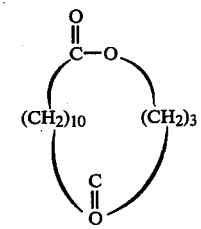

is reduced electrochemically.

12 Claims, No Drawings

PREPARATION OF CYCLOPENTADECANOLIDE

The present invention relates to a novel process for the preparation of cyclopentadecanolide by electrochemical reduction of 12-oxocyclopentadecanolide.

Musk scents are of fundamental importance in the perfume industry. Cyclopentadecanolide, a musk scent which occurs naturally in angelica, possesses a musk note which is one of the most delicate, and one of the most desirable, in the perfume industry. There has therefore been no lack of attempts to prepare cyclopentadecanolide industrially.

Thus, for example, attempts have been made to cyclize 15-hydroxypentadecanoic acid or 15-halopentadecanoic acid to give cyclopentadecanolide (cf. for example M. H. Klowen and J. G. J. Kok, Parfümerie und Kosmetik 43 (1962), 35; G. Ohloff, La France et ses parfums 1970, 146; and S. Abe, T. Eto and J. Tsujito, Cosmetics and Perfumery 88 (1973), 67). The cyclization is carried out on the Rugglie-Ziegler dilution principle, and the space/time yields are therefore very unsatisfactory. Moreover, the substituted pentadecanoic acid derivatives required are obtainable only by expensive multi-stage syntheses. German Published Application DAS 2,731,543, and the publications mentioned therein, describe cyclopentadecanolide syntheses which use 13-oxabicyclo[10.4.0]-hexadec-1(12)-ene as a starting material. The disadvantage of these processes is that the yields are unsatisfactory in many cases, or that peroxides have to be used. Moreover, the steps of conversion to an oximino-lactone, subsequent reductive ring opening to give 15-hydroxypentadecanoic acid and, finally, thermal cyclization to give cyclopentadecanolide represent a very expensive and industrially unsatisfactory synthesis route.

12-Oxocyclopentadecanolide would be a suitable intermediate for the synthesis of cyclopentadecanolide if it were possible to reduce the carbonyl group in the 12-position selectively to the methylene group. All prior attempts in this direction, such as the Clemmensen reduction using zinc amalgam (U.S.S.R. Pat. No. 521,274), or conversion to a tosylhydrazone followed by fragmentation (J. R. Mahajan and H. Aranjo, Synthesis 1980, 64), have, however, given only moderate yields.

We have found that cyclopentadecanolide of the formula

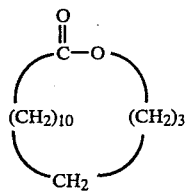

I can be particularly advantageously obtained by the electrochemical reduction of 12-oxocyclopentadecanolide of the formula

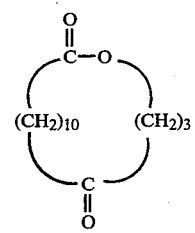

II

The electrochemical reduction is carried out in a conventional industrial electrolysis cell, for example in a compartmented cell which has the form of a filter press. The diaphragm used may be, for example, a cation exchanger membrane, and the electrolyte in the novel process is a solution of II in a conductive system, or an emulsion of II employing a conductive system. For example, II may be dissolved in an alcohol, e.g. methanol, ethanol, isopropanol or butanol, an ether, e.g. dioxane, tetrahydrofuran or a diglycol or an oligomeric glycol, or a hydrocarbon, e.g. toluene or xylene. Preferred conductive systems are acids which may contain water, for example sulfuric acid, hydrochloric acid, sulfonic acids or $HBF_4$. Examples of suitable cathode materials are platinum and other noble metals, mercury, lead, nickel, zinc and graphite, but cadmium is preferred. The electrolysis is carried out, for example, at a current density of from 1 to 50 $A/dm^2$, in particular of from 3 to 10 $A/dm^2$, and at, for example, from $-20°$ to $+95°$ C. The conversion of II can be varied within wide limits, but it is preferable to carry out the electrolysis so that more than 30% of II is converted. Unreacted II can be recycled to the electrolysis. The material discharged from the electrolysis is worked up by a conventional method, for example by distillation or extraction. The process can be carried out either batchwise or continuously.

The Examples which follow illustrate the process according to the invention.

EXAMPLES 1 TO 7

The electrolysis is carried out in a compartmented cell having a cation exchanger membrane. The surface area of the electrode is 1 $dm^2$. A $PbO_2$ anode is used, and the anolyte is 30% strength sulfuric acid. The electrolysis is carried out with 6 F per mole of II. Further details of the experiments are summarized in the Table below. During the electrolysis, the catholyte and the anolyte are each pumped through a heat exchanger. After the electrolysis is complete, the catholyte is charged onto 1.5 l of ice water, and thereafter the mixture is extracted twice with methylene chloride and twice with methyl tert.-butyl ether, the organic phases are combined, washed neutral with sodium bicarbonate and dried, and the solvent is distilled off. The residue is weighed, the contents of II and I are determined by gas chromatography, and the conversion of II and the yield of I are calculated from these measurements. The results are also summarized in the Table below.

| Example | Cathode | Catholyte | T (°C.) | I (A/dm²) | Uc (V) | Product Amount (g) | Content (determined by gas chromatography) II (%) | I (%) | Conversion of II (%) | Yield of I (%) |
|---|---|---|---|---|---|---|---|---|---|---|
| 1 | Cd | 77 g of II<br>684 g of CH₃OH<br>77 g of H₂SO₄, 30% | 17–20 | 5 | 10.5–13.0 | 67.5 | 20.3 | 50.6 | 82 | 58 |
| 2 | Cd | 77 g of II<br>884 g of dioxane<br>300 g of H₂SO₄, 30% | 24–25 | 5 | 9.0–13.2 | 72.0 | 23.5 | 70.6 | 78 | 90 |
| 3 | Cd | 77 g of II<br>684 g of CH₃OH<br>77 g of HBF₄, 35% | 24–25 | 5 | 7.0–10.0 | 62.1 | 32.9 | 61.8 | 74 | 72 |
| 4 | Zn | 77 g of II<br>684 g of CH₃OH<br>77 g of H₂SO₄, 30% | 23 | 5 | 12.6 | 70.8 | 72.2 | 27.8 | 34 | 81 |
| 5 | Pb | 77 g of II<br>684 g of CH₃OH<br>77 g of H₂SO₄, 30% | 20–22 | 5 | 13.8–14.0 | 72.0 | 82.2 | 16.2 | 23 | 70 |
| 6 | Hg | 12.6 g of II<br>112 g of CH₃OH<br>12.6 g of H₂SO₄, 30% | 18–19 | 2.7 | 14.0–19.0 | 12.0 | 90.8 | 5.0 | 13 | 37 |
| 7 | Pt | 77 g of II<br>684 g of CH₃OH<br>77 g of H₂SO₄, 30% | 21–24 | 5 | 12.8–13.2 | 71.8 | 91.9 | 4.1 | 14 | 28 |

I: current density
Uc: cell voltage
T: electrolysis temperature
II: 12-oxocyclopentadecanolide
I: cyclopentadecanolide

We claim:

1. A process for the preparation of cyclopentadecanolide of the formula

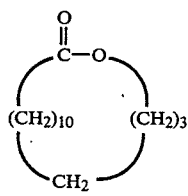

which comprises:
electrochemically reducing 12-oxocyclopentadecanolide of the formula

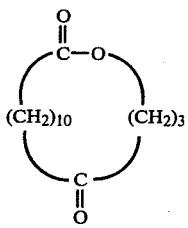

in an electrolytic cell at a current density of from 1 to 50 A/dm² and at a temperature of from −20° to +95° C.

2. A process as claimed in claim 1 wherein the electrochemical reduction is carried out at a current density of from 3 to 10 A/dm².

3. A process as claimed in claim 1 wherein the electrochemical reduction is carried out to achieve a conversion of the compound II of more than 30%.

4. A process as claimed in claim 1 wherein the electrochemical reduction is carried out in an acid electrolyte and on an electrode selected from the group consisting of platinum and other noble metals, cadmium, mercury, lead, nickel, zinc and graphite.

5. A process as claimed in claim 1 wherein the electrochemical reduction is carried out in a compartmented electrolysis cell having a cation exchanger membrane as the diaphragm between the anodic and cathodic compartments.

6. A process as claimed in claim 5 wherein the cathode is a cadmium electrode.

7. A process as claimed in claim 6 wherein the electrochemical reduction is carried out at a current density of from 3 to 10 A/dm².

8. A process as claimed in claim 6 wherein the conducting electrolyte is a mixture of water and sulfuric acid.

9. A process as claimed in claim 6 wherein the conducting electrolyte is a mixture of water and HBF₄.

10. A process as claimed in claim 8 wherein the compound II is dissolved in an organic solvent selected from the group consisting of methanol and dioxane.

11. A process as claimed in claim 1, wherein the electrochemical reduction is carried out in an acid electrolyte.

12. A process as claimed in claim 1, wherein the electrochemical reduction is carried out on a cadmium electrode.

* * * * *